United States Patent [19]

Grifols Lucas

[11] Patent Number: 5,549,866
[45] Date of Patent: Aug. 27, 1996

[54] PROCESS OF MAKING A FLOW REGULATION DEVICE

[76] Inventor: Victor Grifols Lucas, Poligono Levante-Can Guasch, s/n, 08150 Parets Del Valles, Barcelona, Spain

[21] Appl. No.: 263,755

[22] Filed: Jun. 22, 1994

Related U.S. Application Data

[63] Continuation-in-part of Ser. No. 844,843, Mar. 2, 1992, abandoned.

[30] Foreign Application Priority Data

Mar. 18, 1991 [ES] Spain ................................ 9100691

[51] Int. Cl.⁶ .................................................. B29C 67/00
[52] U.S. Cl. ............................................ 264/451; 264/320
[58] Field of Search ............................... 264/25, 26, 320, 264/451

[56] References Cited

U.S. PATENT DOCUMENTS

| | | | |
|---|---|---|---|
| 2,686,337 | 8/1954 | Kaufman | 264/26 |
| 4,381,591 | 5/1983 | Barger et al. | |
| 4,743,235 | 5/1988 | Waldbillig et al. | |

FOREIGN PATENT DOCUMENTS

| | | |
|---|---|---|
| 160807 | 3/1985 | European Pat. Off. |
| 2932982 | 8/1979 | Germany |
| 689081 | 3/1953 | United Kingdom |
| 712852 | 8/1954 | United Kingdom |
| 2254169 | 3/1992 | United Kingdom |
| WO80/00123 | 2/1980 | WIPO |

*Primary Examiner*—Leo B. Tentoni
*Attorney, Agent, or Firm*—Darby & Darby, P.C.

[57] ABSTRACT

A flow regulator for catheters and similar devices and a process for their manufacture. The regulator consists of a tube having both cross-sectional and longitudinal dimensions of pre-determined precision, the regulator having extended tubular extremities for connecting to the catheter feed system. The manufacturing process includes the insertion of an axially mobile internal rod concentric with the tube, followed by molding stage by flattening the tube around the internal rod which is inside the tube, high frequency heating of the tube around the internal rod to heat internal regions of the tube, and then, after suitable cooling period has elapsed, withdrawing the internal rod to leave the tube with its precisely dimensioned bore.

5 Claims, 5 Drawing Sheets

5,549,866

PROCESS OF MAKING A FLOW REGULATION DEVICE

CROSS-REFERENCE TO COPENDING APPLICATIONS

This is a continuation-in-part of U.S. Ser. No. 07/844,843, filed Mar. 2, 1992, now abandoned.

FIELD OF THE INVENTION

This invention relates to a device for controlling the flow in catheters and other similar equipment and a process for manufacturing the device.

BACKGROUND OF THE INVENTION

Conventionally, the precise control of fluid to be administered by means of a catheter to the human body presents major difficulties because of the small flow required to be controlled and which must be easily adjustable.

Several systems are known among which is that consisting of a progressive throttling of the tube either by a lateral or diametric compression or by the introduction of a body which effects the partial blockage of the tube. Also known is the method of longitudinal extension of the tube which closes in on an internal solid nucleus thus reducing the cross sectional passage for the fluid within the tube.

Conventional systems provide a defective and erratic progression of the flow graduation in view of the small passage of flow and also create the possibility of liquid particles being caught in these small passages thus changing the flow conditions after the flow has been adjusted to the required rate.

Such defects result in a lack of reliability of the operation of the flow control during its use, both as to regulation and flow conditions. As a consequence, variations occur when used to administer flow control in medical treatment.

Apart from the possibility of throttling, which may be suitable for large diameter tubes that can be adjusted by squeezing their walls together, the use of a very small hydraulic radius flow regulation device is required, leading to the presence of extremely small interstices that give rise to the previously mentioned defects.

The present invention is a device for regulating and controlling the flow in catheters and similar equipment, designed to obviate the defects mentioned above.

SUMMARY OF THE INVENTION

The present invention is directed to a method and apparatus for manufacturing a flow regulation device. The invention involves ensuring that an internal rod is arranged within a tube and substantially coaxial with a longitudinal axis of the tube by means of a guide member that is within an open end of the tube, molding a portion of the tube around the internal rod by applying pressure to the portion of the tube and high frequency heating the portion of the tube, the high frequency heating causing internal regions of the portion of the tube to heat while the applied pressure keeps a cross-section of the internal regions circular throughout an entire duration of the high frequency heating and yet avoids causing an outside surface of the tube from becoming semi-molten, extracting the internal rod from the portion of the tube, and extracting the guide member from the open end of the tube, whereby the molded portion of the tube constitutes the flow regulation device.

BRIEF DESCRIPTION OF THE DRAWINGS

For a better understanding of the present invention, reference is made to the following description and accompanying drawings, while the scope of the invention is set forth in the appended claims.

DESCRIPTION OF THE PREFERRED EMBODIMENT

Figure 1:
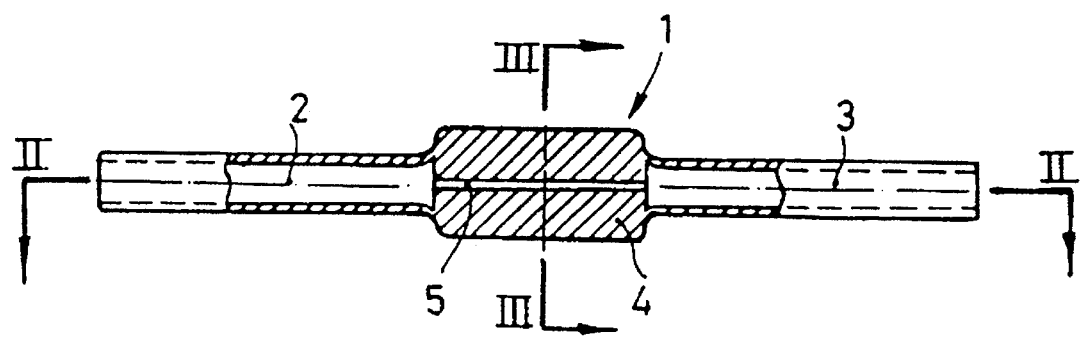
FIGS. 1 and 2 show longitudinal sections of a flow regulator device in accordance with the present invention.
Figure 2:
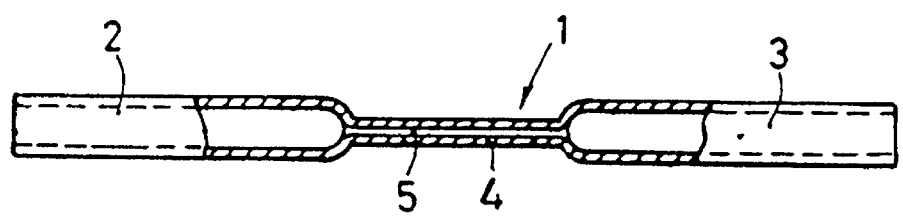

As may be seen in FIG. 1, the flow regulator of the present invention consists essentially of a single molded piece 1, with tubular extremities 2 and 3 and a central body 4 pierced with a hole forming the bore 5 that regulates the flow. The bore 5 preferably has a circular cross-section or a cross-section that is generally circular in order to obtain the maximum transverse dimensions for a given hydraulic radius. The diameter of the bore 5 is of high precision.

Figure 3:
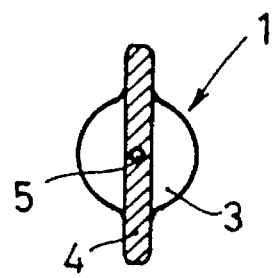
FIG. 3 shows a transverse section take across section III—III of FIG. 1.

The central body 4 is shown as flattened (see FIGS. 1 and 3) to facilitate manufacture but other exterior shapes would be acceptable provided the interior bore 5 remains cylindrical or of a general cylindrical form.

Figure 4:
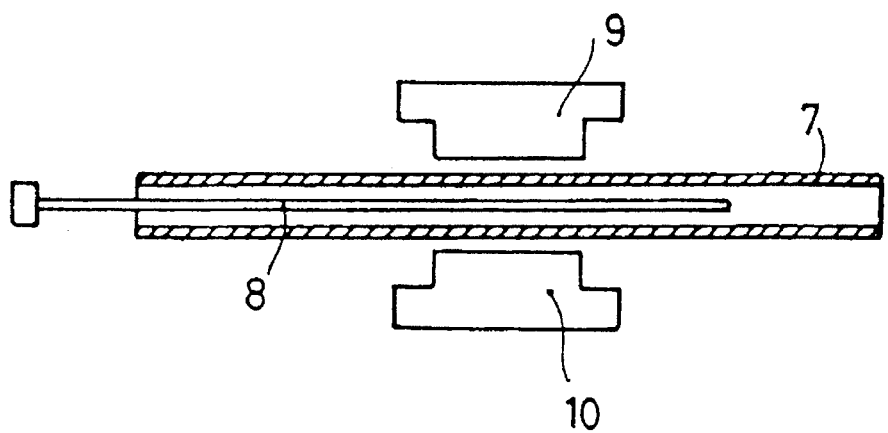
FIGS. 4, 5 and 6 show diagrammatic views of three distinct phases in the manufacture of the flow regulator device of FIGS. 1–3.
Figure 5:
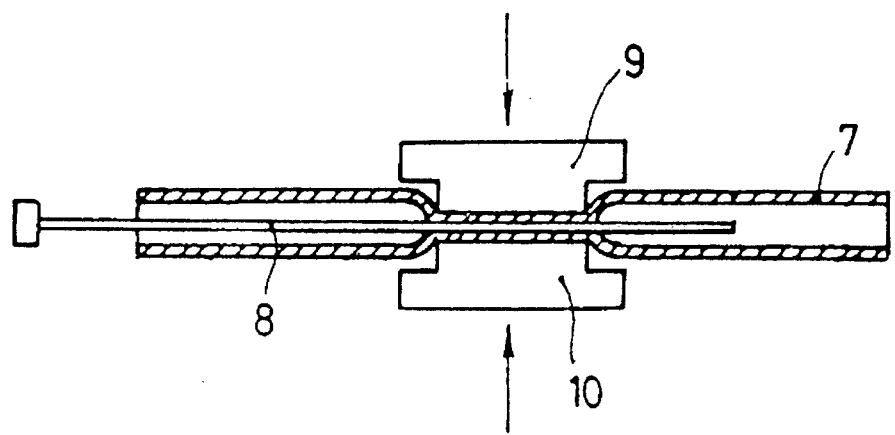
Figure 6:
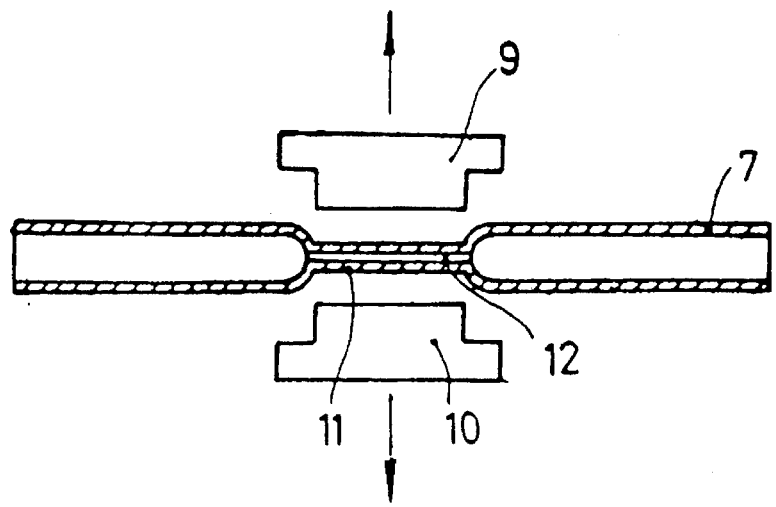
Figure 7:
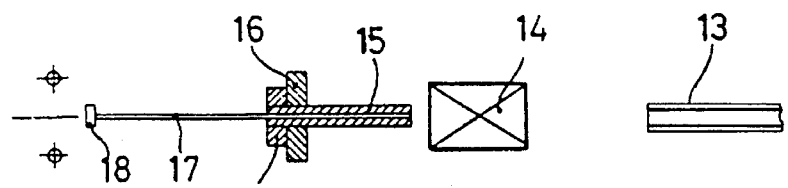
FIGS. 7 through 13 show diagrammatic views of various phases in manufacture of the flow regulator device of FIGS. 1–3 with the position of a calibrated internal rod in relation to the body of the flow regulator device being formed.
Figure 8:
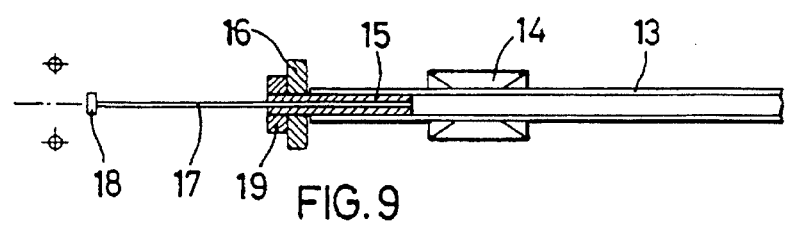

Manufacture of the flow regulation device which has the bore for passage of the fluid and the process for providing the passage is shown schematically in FIGS. 4, 5 and 6. In FIG. 4, the tube 7 is shown in its initial state with a mandrel or calibrated internal rod 8 within its spatial interior and with tooling fixtures 9 and 10 exterior of the tube 7. These tooling fixtures may be considered a molding press tool.

In FIG. 4, tooling fixtures 9 and 10 are shown in a position ready for hot pressing after the press tools 9 and 10 act on the tube 7 as shown in FIG. 5 and then high frequency heating takes place. Fixtures 9 and 10 press on opposite sides of the exterior of the tube 7 and cause the interior to adopt the form of the exterior of the calibrated internal rod 8. Following the pressing operation of the tooling on the exterior of the tube 7 by the fixtures 9 and 10 on its central zone 11 shown in FIG. 6, and after an adequate cooling period, the fixtures 9 and 10 can be withdrawn and the internal rod 8 extracted from the tube.

Such a manufacturing operation leaves the tube 7 in its final state for the operation of regulating the fluid to be administered. This final state may be end sections or terminal lengths in simple tubular form as in the initial state and the central zone in some shape (such as flattened 11) depending on the shape of the tooling fixtures 9 and 10 while causing the interior 12 to adopt the form of the fluid passage required.

Figure 9:
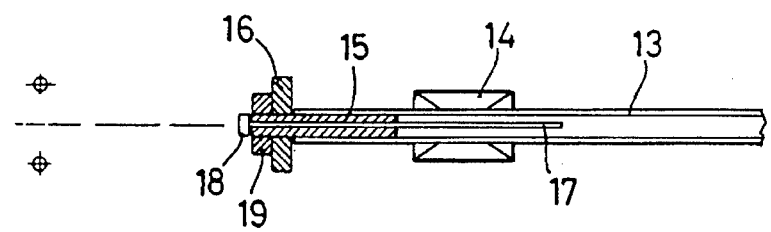

FIGS. 7 through 13 schematically illustrate the successive phases of the manufacturing process for the device for regulating flow such as catheter flow. The drawings show the initial tube 13 to be fed axially to the molding press tool 14 (that may contain the fixtures 9, 10 of FIGS. 4–6). Guide member 15 is opposite the extremity of tube 13 and carries an external stripping or expulsion collar 16. The internal rod 17 is inserted axially into the guide member 15 as shown in FIG. 9, in which the internal rod 17 can be seen to be fully within the tube 13 with its head 18 in contact with a flange or head ring 19 adjacent to the expulsion collar 16.

Figure 10:
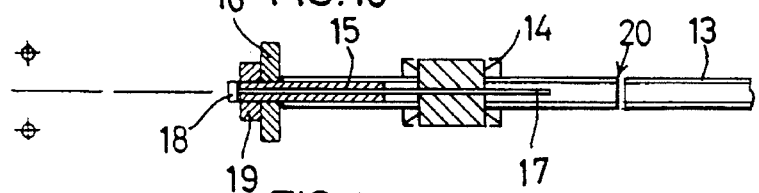
Figure 11:
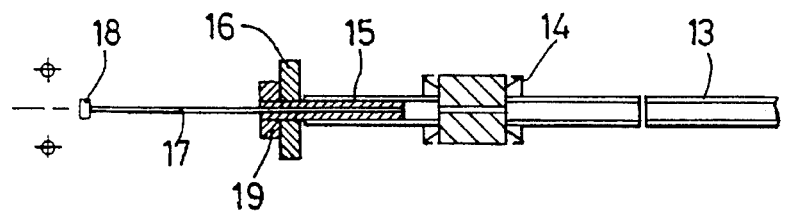
Figure 12:
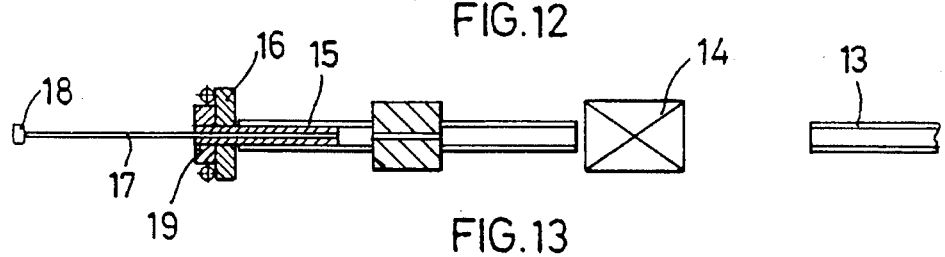
Figure 13:
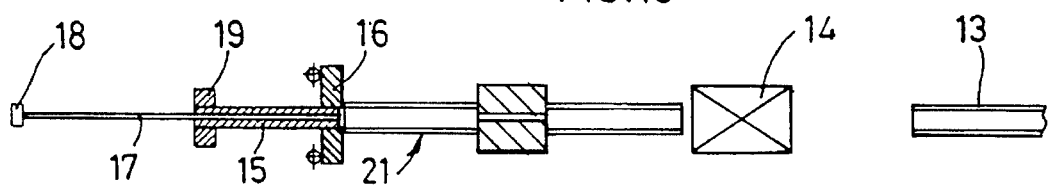

FIGS. 10 and 11 show the stages of molding of the central zone followed by cutting off the tube at a section 20 from the feed length of tube 13. FIG. 11 shows the internal rod 17 extracted from the guide member 15, with the entire regulating device 21 in its finished state shown in FIG. 12 wherein it is separated from the molding press tool 14 and is finally detached by action of the expulsion collar 16 as in FIG. 13, which shows the finished regulating device 21 for regulating flow.

Figure 14:
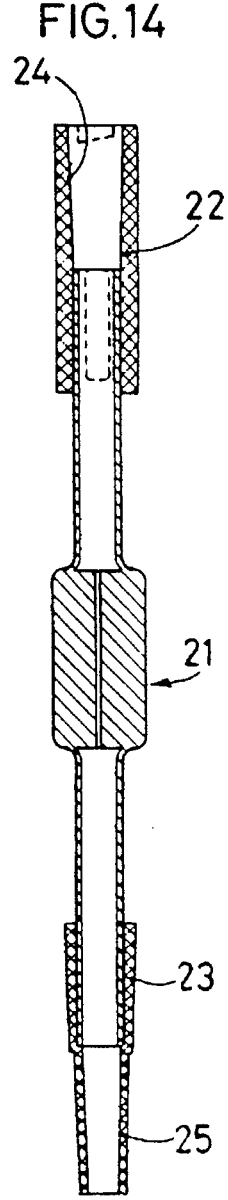
FIGS. 14 and 15 show respectively the flow regulator device of FIGS. 1–3 connected to its associated feed tubes.
Figure 15:
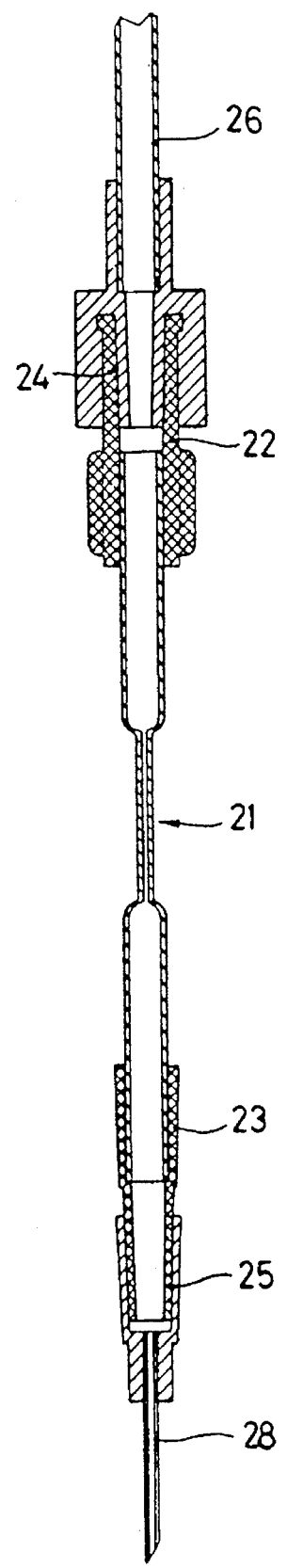
Figure 16:
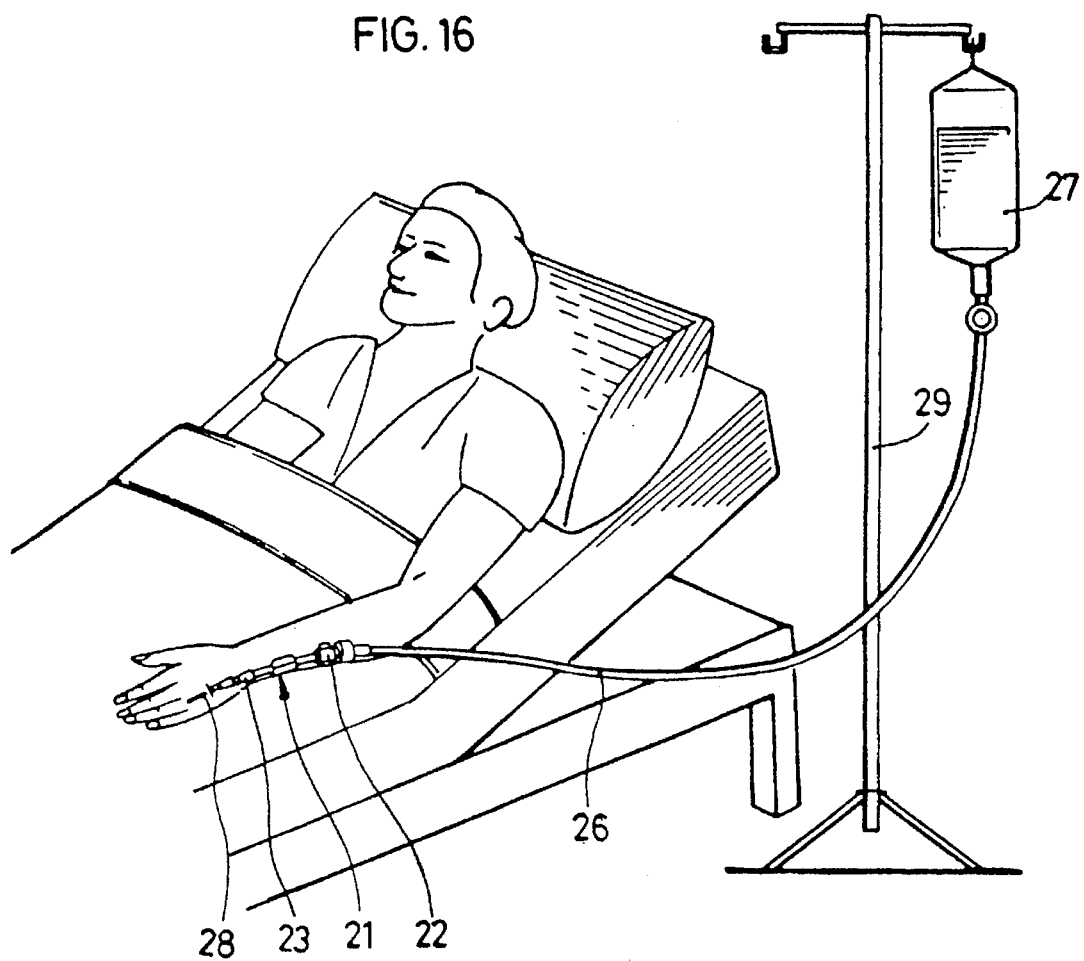
FIG. 16 is a schematic view of the flow regulator device of FIGS. 1–3 employed in clinical operation.

The device 21 is coupled to union pieces 22 and 23 as shown in FIG. 14 and 15. For example, piece 22 has a conical internal housing 24 suitable for accepting the supply tubing system 26, while piece 23 has a section 25 adaptable for connection to a needle 28 or catheter, as shown in FIGS. 15 and 16, to be applied to the patient.

Control of the flow through the control device is governed by the diameter and the length of the bore in the molded zone of the device 21. The control is also governed by the height of the vessel containing the fluid 27 that feeds through the supply tube 26 with respect to the level of the injection point where the catheter or needle 28 is inserted into the vein of the patient. Variation of the liquid column is obtained by variation of the height of the vessel on a conventional extendable support column 29.

Anything not affecting, altering or modifying the essence of the regulator herein disclosed is a variable for purposes of this invention. The flow regulator device of the invention has a fixed bore which produces a constant and controlled flow of fluid wherein the regulator is of high precision and, contrary to conventional practice, non adjustable. By this means, an absolute regularity of the bore is assured with a consequent permanently controlled flow for clinical treatment.

In addition, by using a circular or generally circular passage through of small diameter, the transverse dimensions of the passage are maximized for a given hydraulic radius, thus obviating the very small interstices obtained in conventional systems and which give rise to irregular operation or blockages. The process for manufacturing the flow regulator device according to the invention provides for the production of tubes having bores with individual small dimensions and cross sections which are constant over the whole length. The process is industrially practicable and of low cost.

When supplying infusion liquids to patients from tubes having a restriction, the infusion liquids may contain, according to usual standards, particles which may go up to 25μ. That is, that particles are not visible to the eye. In conventional flow regulating mechanisms in tubes for catheters, the transversal restriction of the cross-section of the tube approaches widths of a few μ, for which reason the larger size particles will be trapped in the squeezed opening. This is of substantial significance, especially for long lasting treatments, which are to be found very frequently in the treatment of patients receiving a medical infusion for a long time. In these cases, the passage becomes progressively, even severely obstructed, changing the flow conditions and, therefore, the medical treatment.

The present invention overcomes this obstruction problem with very specific and very precisely gaged circular tubes for the feeding of the catheters, such as with diameters between 0.1 and 0.3 mm.

Instead of changing the cross-section of a given tube by means of squeezing, the present invention provides the regulation of flow by means of tubes of well gaged constant cross section. In this way, for the same hydraulic radius, the cross section has a much more important dimension, preventing its obstruction and guaranteeing a continuous and reliable feeding of the infusion liquid to the patient. Further, by changing the relation of the length of the tube to its diameter, the effective hydraulic radius is also changed, for which reason the flow conditions may be changed also by changing the length of the precisely gaged passage. Accordingly, various ways are available to change the feeding conditions of the catheters: first, choosing the diameter of the intermediate gaging element, which has a very precise diameter to be appropriate to the desired flow of liquid, and second, choosing a different length of the tube for each diameter. These two ways of changing the effective flow of the infusion are new and very advantageous, allowing the medical personnel to choose beforehand very precise conditions of flow for the infusion, which will be maintained for any duration of the treatment.

The present invention has still another important characteristic, which refers to the process of manufacture, that is, heating with high frequency energy. This is an essential feature if precisely calibrated tubes are to be obtained, because high frequency heating will cause the heating of the internal regions of the starting tube to ensure a regular swagging of the tube and, therefore, the production of a precisely calibrated tube with a diameter of between 0.1 and 0.3 millimeters.

If conventional heating were applied instead, a considerable temperature gradient is created between the outside surface of the tube and its internal parts, which may lead to an excessively high temperature on the outside, so that the material in this area would become semi-molten before forming. With a semi-molten exterior, the tube can not be shaped properly under pressure. Further, the difference in temperature between the inside and outside of the tube may be such that the temperature on the inside would not be sufficient for obtaining a precise circular shaped molding of the bore. In this case, the cross-section of the bore 5 would not be circular, but rather irregular and elongated, failing to obtain a precise calibration for the tube and also failing to prevent the clogging of the lateral restricted portions in the cross-section.

On the other hand, high frequency heating of the tubes depends on the nature of the material because, in order that high frequency can be used for heating purposes, it is necessary that the material have polar characteristics to create internal heating. This aspect distinguishes the present invention over conventional teachings which rely mainly on non polar materials such as polyethylene as a preferable material for the flow restrictor. Polyethylene, being a non polar material, can not be heated by high frequency heating.

High frequency heating allows the internal part of the tube to become heated so as to permit a correct adaptation of the tube to the internal rod without wrinkles or creases, as is the case with heating by radiation or convection from the external surface of the tube. In these cases, the temperature gradient between the external and internal parts of the tube does not allow the attainment of a sufficient fluidity in the internal part of the tube to properly adapt the material to the internal rod. This arises because the external surface cannot be heated sufficiently without arriving to liquid or semi liquid consistence, which prevents the process from continuing further.

In the present invention, the compression tools may operate in one single operation to press and subsequently heat the tube by high frequency. The pressing of the tube on the internal rod is made as a first step of a unique working operation, after which the heating by means of high frequency takes place. The diameter of the internal passages in the present invention may be limited between 10 and 250 microns. Although the parameters which are related to the high frequency heating may be variable, in a preferred embodiment the present invention could use a frequency of 27 Mhz together with a power output of 50–150 W and a welding time of 2 seconds approximately. Concerning the nominal flow rate, the length of the metered passage and the diameter of the passage, the following Table is presented to exemplify flow rate and dimensions attainable in accordance with the invention.

High frequency heating takes place just after beginning the compression of the tube 7. Carrying out the manufacturing process of the invention is done very rapidly; for a substantial part of the cycle of flow regulator manufacture, both compression and high frequency or induction heating overlap. The process is carried out in a fully automatic manner; that is, no manual operations are contemplated. Thus, each step of the process has its own means for completing its task.

TABLE

| NOMINAL FLOW RATE (ml/hour) | LENGTH OF THE METERING PASSAGE (mm) | DIAMETER OF THE METERING PASSAGE μ |
| --- | --- | --- |
| 20 | 16 | 150 |
| 40 | 16 | 180 |
| 65 | 16 | 200 |
| 85 | 16 | 220 |
| 105 | 16 | 230 |
| 125 | 14 | 230 |

The present invention includes very fine tubes operating with very reduced pressures because the fluid flow is only due to gravity forces. At the same time, the inner diameter of the tubes ranges between 50 and 250 microns approximately, that is, the maximum diameter contemplated is about ⅓ of the minimum internal diameter envisioned by some conventional teachings.

The present invention makes it easy for the medical practitioner to control the fluid flow as desired and avoids misadjustments in compression flow restrictors, which conventionally have mechanical means to constrict the tube, making them prone to many misadjustments from the clogging of the very restricted passages obtained by the compression of a tube. Additionally, conventional restrictors, being exposed, are accessible to be manipulated, either accidentally by the patient or intentionally by auxiliary personnel seeking to increase temporarily the previously metered flow of fluid. Such a fluid flow increase is not possible with the present invention, in which the flow of fluid is completely constant and cannot be varied except by changing to another unit with a different gauge. The present invention operates in the range of semicapilarity, with the flow of fluid through the passages of the present invention being inversely proportional linearly to the length of the passage.

With reference to FIGS. 7–13, the process according to the invention will be described by referring to a specific example that includes dimensions. Of course, the invention is in no way limited to such dimensions, which are set forth for illustrative purposes only.

The process starts with a PVC robe 13 having an outside diameter of 4.1 millimeters and an inside diameter of three millimeters. The guide member 15, exemplified by a tubular mandrel, will be displaced toward the PVC robe 13 and inserted into the interior space of the PVC tube 13. This allows for the transport of the tube 13 to the molding press tool 14, exemplified by a working head. The assembly of the guide member 15 and its expulsion collar 16, exemplified by a support, travel backwards to the end of the molding press tool 14, carrying the tube 13 until it becomes placed within the molding press tool 14 containing the electrodes.

The end of the internal rod 17 is then pushed out of the guide member 15, becoming introduced inside of the PVC tube 13, as shown in FIG. 9. The internal rod 9, for example, has a diameter of 0.15 millimeters.

The electrodes contained in the molding press tool 14 simultaneously serve as pressure molding parts and, for example, have a length of sixteen millimeters. They are applied under pressure onto the tube 13. The pressure may be applied by any conventional means, preferably by pneumatic pressure cylinders. The pressure force is exemplified by an amount of 16 Kgf.

After compression of the tube 13 by the pressure molding parts, high frequency pulses are applied for an approximate time span of two seconds at a frequency of 27 megahertz. This produces a melting down of the PVC tube 13. The high frequency pulses may be applied by the electrodes, which also serve as the pressure molding parts themselves as previously mentioned.

After a short cooling down period of time, for instance four seconds, the guide member 15 is withdrawn. After this withdrawal, the tube is cut to a desired length. Subsequently, the pressure molding parts, which simultaneously serve as the electrodes for the application of the high frequency pulses, will be released. The guide member 15 will then be removed and the manufactured part 21 (such as a desired flow regulation device) will be expelled from the guide member 15 because of its abutment on the expulsion collar 16, which is exemplified as a flange.

The precise values given for the various parameters pertain to this example of the invention. The outside diameter of the PVC tube may vary, for example between 2 and 5 mm, and the internal diameter may vary, for example between 1 and 5 mm, and still provide satisfactory results as attained by the present example. The same could be said as to the travel of the guide member 15, which could vary within ample limits depending on the length of the part to be manufactured. The same may be said as to the force applied by the pressure elements, which could vary approximately within a range of 10 to 20 Kgf.

While the foregoing description and drawings represent the preferred embodiments of the present invention, it will be understood that various changes and modifications may be made without departing from the spirit and scope of the present invention.

What is claimed is:

1. A method of manufacturing a flow regulation device, comprising the steps of:

providing a guide member within an open end of a tube;

inserting a rod through said guide member and into said tube whereby said guide member maintains said rod coaxial with the axis of said tube, said rod having a smaller external diameter than an internal diameter of said tube;

molding a portion of the tube around the rod by keeping a cross-section of internal regions of the portion of the tube circular through an entire duration of the step of molding and preventing an outside surface of the tube from becoming semi-molten throughout the entire duration of the step of molding, pressing the portion of the tube on the rod and high frequency heating the portion of the tube; and extracting the rod and guide member, whereby the molded portion of the tube that remains constitutes the flow regulation device.

2. A method as in claim 1, wherein the portion of the tube is composed of a material having polar characteristics.

3. A method as in claim 1, wherein the step of high frequency heating is performed to permit correct, precise adaptation of the portion to the internal rod.

4. A method as in claim 1, wherein the step of high frequency heating is conducted in a single operation subsequent to the pressing of the portion of the tube on the rod.

5. A method as in claim 1, further comprising the steps of introducing the guide member into the open end of the tube, introducing the rod through the guide member and into the tube and pressing the tube on the rod, both the steps of introducing and the step of pressing being carried out before the step of high frequency heating.

* * * * *